United States Patent
Bohak et al.

[11] Patent Number: 5,168,058
[45] Date of Patent: Dec. 1, 1992

[54] CELL CULTURE CARRIERS AND METHOD OF USE

[75] Inventors: Zvi Bohak, Rehovot; Avinoam Kadouri, Petach Tikva, both of Israel; Nicholas G. Maroudas, London, England

[73] Assignee: Yeda Research and Development Company, Ltd., Rehovot, Israel

[21] Appl. No.: 544,012

[22] Filed: Jun. 27, 1990

Related U.S. Application Data

[63] Continuation of Ser. No. 34,272, Apr. 3, 1987, abandoned.

[51] Int. Cl.$^5$ .......................... C12N 5/06; C12N 3/04
[52] U.S. Cl. .................... 435/240.23; 435/285; 435/310; 210/150; 261/DIG. 72
[58] Field of Search .............. 435/240.23, 240.241, 435/240.243, 284, 285, 296, 297, 310, 313, 174, 180, 181, 177; 261/94, DIG. 72; 210/150; 55/456, 457

[56] References Cited

U.S. PATENT DOCUMENTS

| | | | |
|---|---|---|---|
| 2,602,651 | 4/1952 | Cannon | 261/DIG. 72 |
| 2,949,934 | 8/1960 | Schrenk | 261/DIG. 72 |
| 3,167,600 | 1/1965 | Worman | 261/DIG. 72 |
| 3,365,180 | 1/1968 | Lerner | 261/DIG. 72 |
| 3,740,321 | 6/1973 | Pagano et al. | 435/285 |
| 3,853,712 | 12/1974 | House et al. | 435/285 |
| 3,941,661 | 3/1976 | Noteboom | 435/285 |
| 4,024,020 | 5/1977 | Weiss et al. | 435/240.23 |
| 4,224,257 | 9/1980 | Robinson | 261/DIG. 72 |
| 4,317,886 | 3/1982 | Johnson et al. | 435/285 |
| 4,343,904 | 8/1982 | Birch et al. | 435/240.23 |
| 4,670,149 | 6/1987 | Francis | 210/150 |
| 4,689,301 | 8/1987 | Adet et al. | 435/240.23 |

FOREIGN PATENT DOCUMENTS

| | | |
|---|---|---|
| 1147679 | 6/1983 | Canada . |
| 0227885 | 10/1985 | Fed. Rep. of Germany ... 261/DIG. 72 |
| 1057084 | 11/1983 | U.S.S.R. ............ 261/DIG. 72 |
| 2178447 | 2/1987 | United Kingdom ............ 435/285 |

Primary Examiner—Robert J. Warden
Assistant Examiner—William H. Beisner
Attorney, Agent, or Firm—Maksymonko & Slater

[57] ABSTRACT

The invention relates to packing material for use in the cultivation of anchorage-dependent cells, which require a solid surface for proliferation. The packing material of the invention is provided in the form of units of curved sheet material, which individual units generally have a thickness of about 0.05 mm to 0.25 mm, the other dimensions being of the order of one to a few millimeter maximum dimensions. Various shapes can be used, such as twisted rectangles, segments of cylinders, convulated ribbons, twisted shapes, ring shape and the like.

2 Claims, 5 Drawing Sheets

CELL CULTURE CARRIERS AND METHOD OF USE

This is a continuation of application Ser. No. 07/034,272 filed Apr. 3, 1987 now abandoned.

BACKGROUND OF THE INVENTION

Most cells including normal tissue derived primary cells are anchorage-dependent, and require a solid surface in order to proliferate, metabolize nutrients and produce biomolecules. Conventional means for growth of these cells on a small scale include petri-dishes, flasks and roller bottles. A number of approaches have been taken by various investigators to develop cell reactors with large surface-area-to-volume ratios for space and operational economy. Such devices include polymer sponge materices, multiple tubing, stacked-plate systems, coiled plastic sheets, microcarrier suspension culture and hollow-fibers. Another approach is to culture cells on a packing material inside a column shaped vessel. One of these systems uses glass beads designed for large scale cell cultivation. Another packing material has a "saddle" shape.

The packing substratum must have several properties:

i. To enable the attached cells to spread to their optimal size and shape in order to metabolize and proliferate;

ii. To promote exchange of metabolites between the cells and the culture medium, by providing an increased ratio of surface to volume inside the packed vessel;

iii. To facilitate medium flow to the cells by providing an increased ratio of surface to volume inside the packed vessel;

iv. To maintain high cell density for long periods, for the production of various biomolecules, even in serum free media.

SUMMARY OF THE INVENTION

According to this invention these requirements for bulk cell culture are provided by random packing of non-interconnected elements which have a planar but curved geometry. Specifically, the shapes that can be used are: planar rings (Raschig's rings), split rings, planar helices, propellor shape, spiral helices, and twisted rectangular films, sheets, or the like. Such packing elements can be fabricated from plastic polymers, preferably transparent, such as polystyrene, polypropylene, and polyester.

DESCRIPTION OF THE PREFERRED EMBODIMENT

Figure 1:
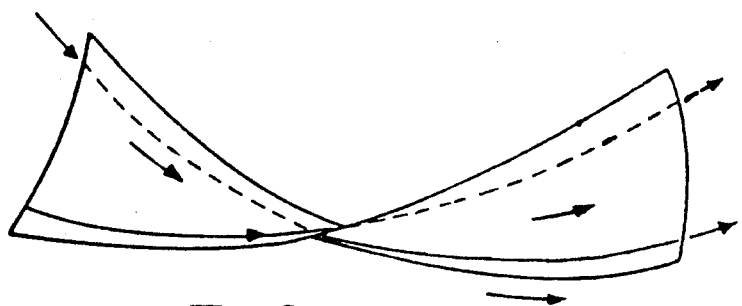
FIG. 1 is perspective view of one embodiment of the packing material of the present invention depicting a linear twisted planar helix packing material.

The specific geometry of the packing material can be obtained by rotary deformation of a plane sheet or ribbon. For example:

1. The linear twisted planar helix (FIG. 1). This consists of a length of flat ribbon which has been twisted into a helical shape around its longer axis. Three advantages result from this geometry in cell culture:

i. Improved spreading and alignment of cells due to the predominantly flat, curved plane geometry.

ii. Improved physiocochemical hydrodynamics, due to the helical flow pattern which is both open and twisted (FIG. 1). The flat planar geometry enables easy viewing of cells (if the polymer is transparent).

Figure 2:
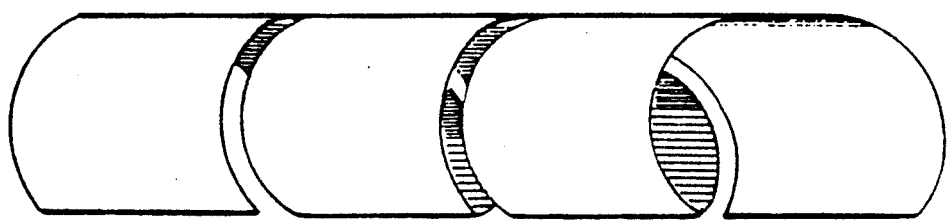
FIG. 2 is a perspective view of another embodiment of the present invention depicting a cylindrical planar helix packing material.

2. The cylindrical planar helix (FIG. 2).

Figure 3:
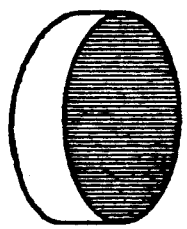
FIG. 3 is a perspective view of another embodiment of the present invention depicting a cylindrical segment packing material.

3. The cylindrical segment (FIG. 3) often hollow.

Figure 4:
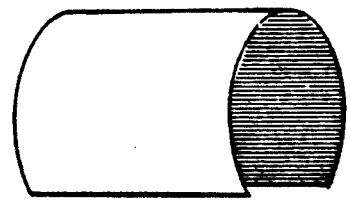
FIG. 4 is a perspective view of another embodiment of the present invention depicting a split ring packing material.

4. Split ring (FIG. 4).

These planar packing elements are superior to solid spheres in the following respects:

i. Larger area for cells to spread, for equal mass of packing material;

ii. Larger surface for mass transfer for equal volumes of packing elements.

iii. Better hydrodynamic flow and mixing;

iv. Less weight for equal surface area of packing material due to low solid volume;

v. Greater transparency, lower optical refraction due to thinner and planar surfaces;

vi. It can be easily sampled for microscopic examination and for determination of cell numbers;

vii. Packing elements are readily made from plastic films of ribbon by standard techniques of hot pressing, stamping, rolling, twisting and cutting. Alternatively, the same shape can be cut from continuous extrusions;

Suitable plastics are polystyrene, polypropylene and polyester which can be surface treated for cell adhesion, by various methods well known in the literature.

The suitable dimensions of these elements are:

Film thickness 0.05 mm to 0.25 mm, length of each unit 2 mm or greater, width or diameter 1 mm to 5 mm.

Such planar packing units are suitable mainly for use as filling of column type reactors with medium perfusion. They can also be used as packing in roller bottles.

In practical implementation of the invention, any tendency for nesting of some embodiments of packing elements can be countered by appropriate installation with or without agitation or other attitude adjustment/variation and/or by assuring variety of precise geometry, and/or by mixing elements of different embodiments in the same chamber, or any combination thereof.

EXAMPLES

1. The materials used for cell culture were passed through a discharge from a plasma torch then washed with methanol, dried and sterilized under UV light. Before cells seeding the carrier was immersed in a solution of 100 ug/ml of poly-D-lysine and rinsed with sterile water.

2. Polystyrene and polypropylene beads, flat squares, cylinders and twisted ribbons having the same computed surface area were placed with Dulbecco's modified Eagle's medium (DMEM) supplemented with 10% fetal calf serum (FCS) in a test tube and seeded with the same number of cells. Twenty-four (24) hours after seeding, cell adherence was determined by trypsinization (Table 1).

Figure 5:
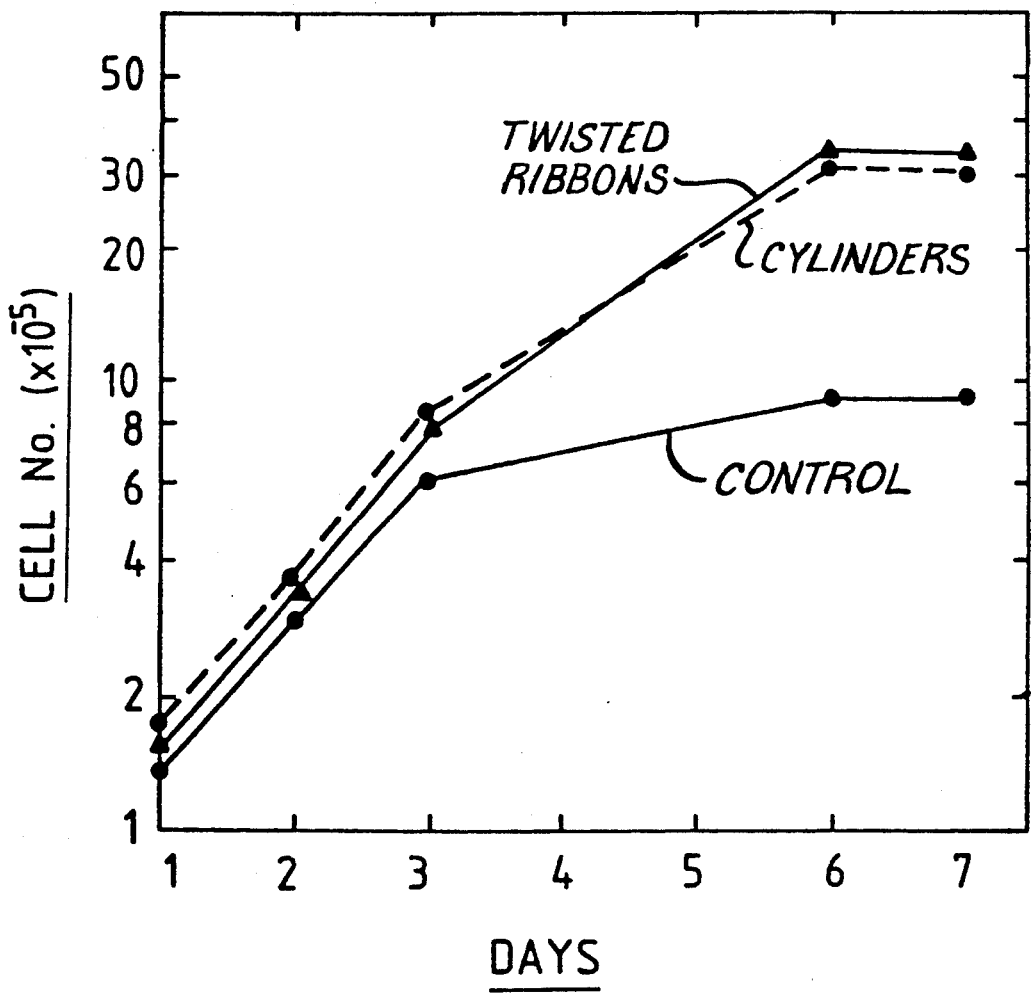
FIG. 5 is a graphic representation of cell proliferation in connection with cylinders and twisted ribbon packing materials of the present invention.

3. Polystyrene cylinders and twisted ribbons having a surface area of about 60 cm$^2$ were placed in test tubes and covered with culture medium. They were seeded with $1.5 \times 10^5$ cells and left overnight at 37° C. to allow the cells to attach. The preseeded supports were then transferred to a siliconized petri-dish and cell proliferation was monitored. Tissue culture plates were used as control. Cells reached $5-6 \times 10^4$ cells/cm$^2$, the same surface density as obtained on petri-dishes (FIG. 5).

Figure 6:
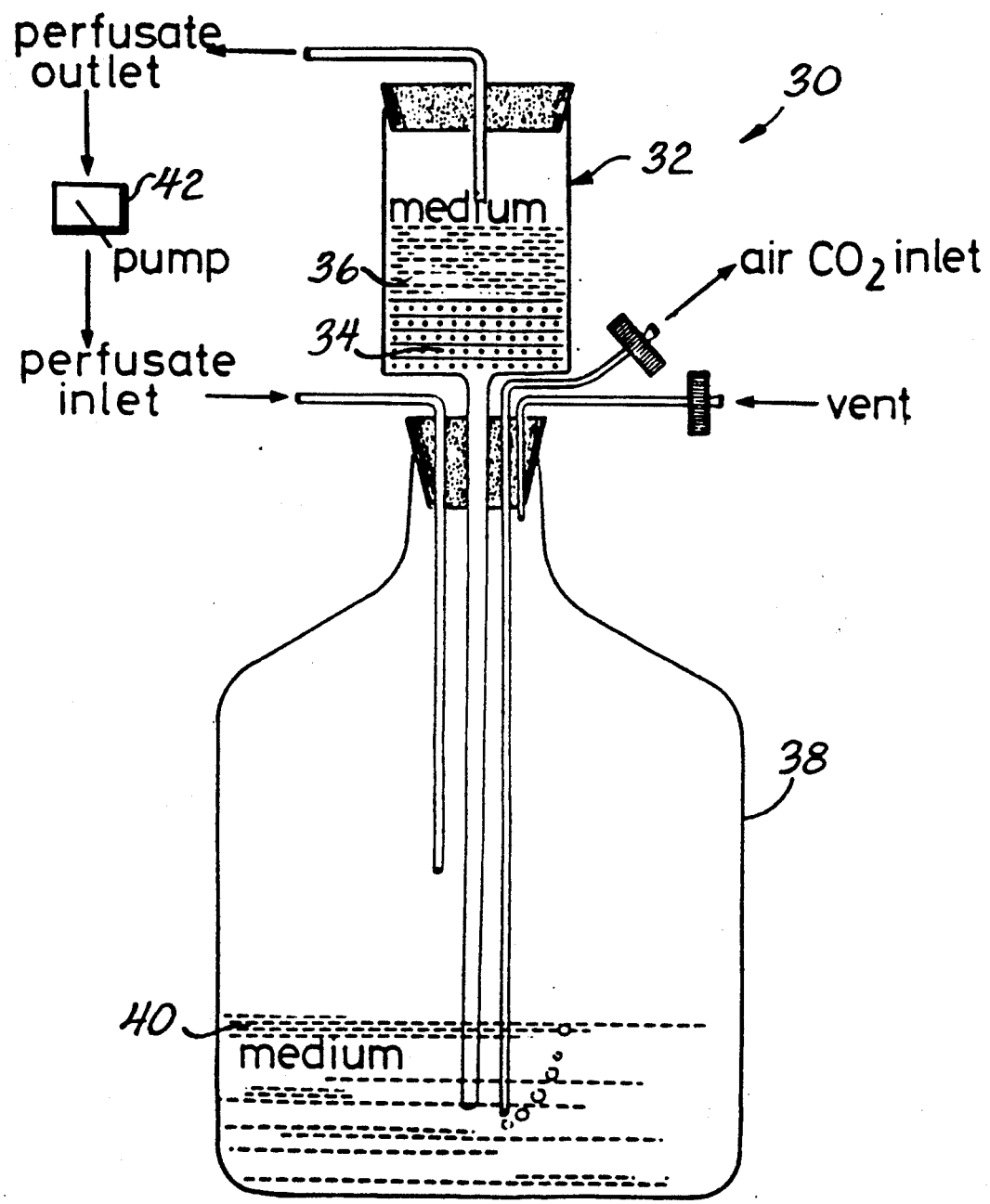
FIG. 6 is a front elevation view of a laboratory scale reactor assembly used to ascertain the efficacy of the present packaging materials.
Figure 7:
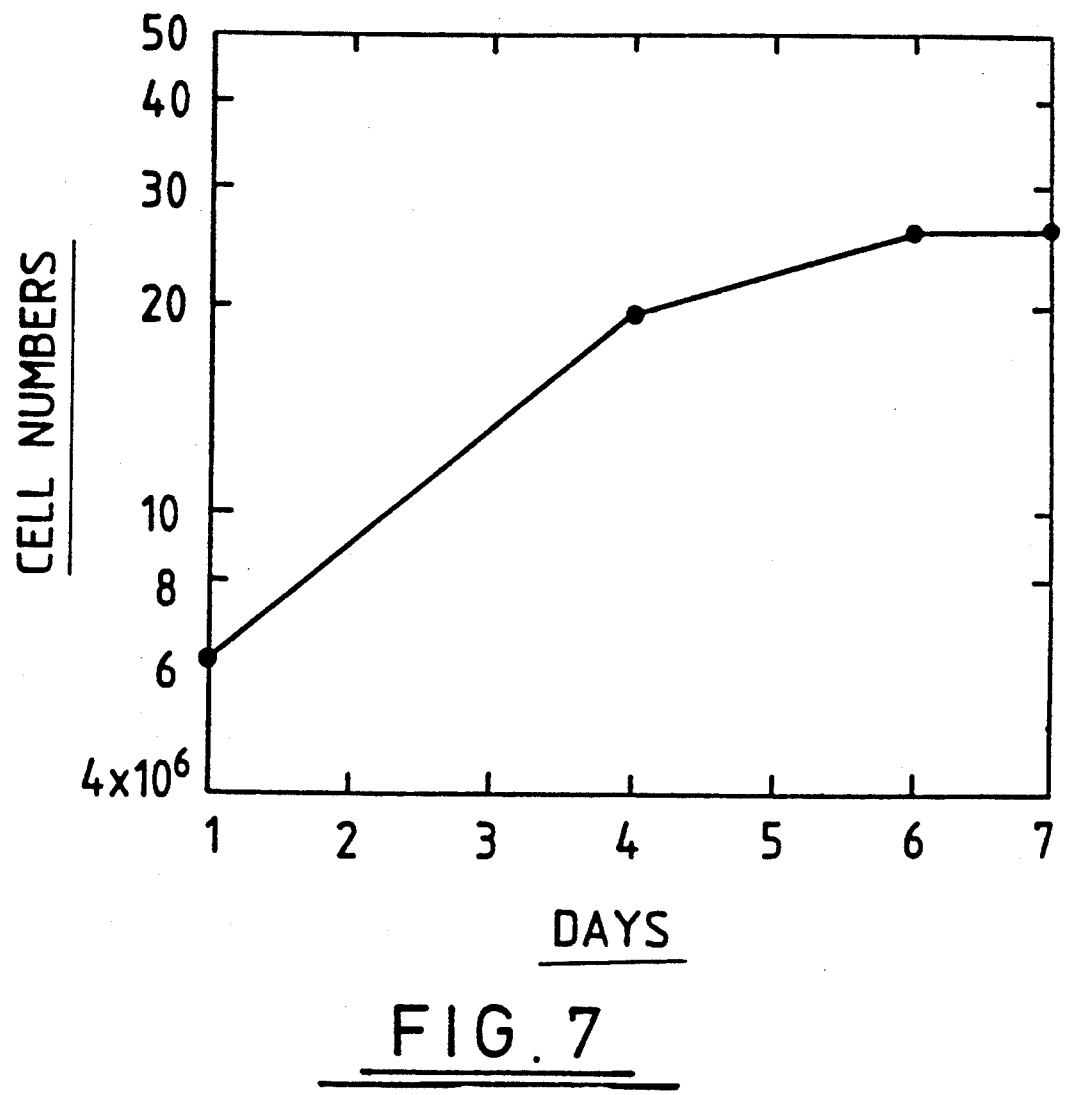
FIG. 7 is a graphic representation of cell proliferation of packing materials of the present invention tested in the reactor assembly of FIG. 6.

4. Cell proliferation on polystyrene cylinders and twisted ribbons having the same surface area was tested in a stationary column reactor. A laboratory scale reactor assembly 30 is depicted in FIG. 6. The carrier was placed in plastic test tubes, covered with culture medium and seeded with human diploid fibroblasts cells. The tubes were rotated ⅓ turn every 5 minutes to allow the cells to settle and spread evenly over both sides of the carrier units. After 18 hours the carrier with the attached cells was transferred to the column reactor 32. The carrier 34 was covered with medium 36. The reservoir 38 was then filled with medium 40 and medium circulation was started. Pump 42 speed was adjusted to give an initial medium residence time of 20 minutes. As the cells proliferated, pumping rate was increased to decrease residence time to 5 minutes. The reactor chamber 32 was sampled periodically by taking out pieces of the cell carrier for cells number determination (FIG. 7). At confluency cell density reached $5-6 \times 10^4$ cells/cm$^2$ and $0.7 \times 10^6 - 2 \times 10^6$ per ml of reactive volume, depending on the density of the packing material.

Figure 8A:
FIGS. 8a, 8b are photographs illustrating cell proliferation on both sides of a carrier sample taken from the reactor vessel of FIG. 6.
Figure 8B:
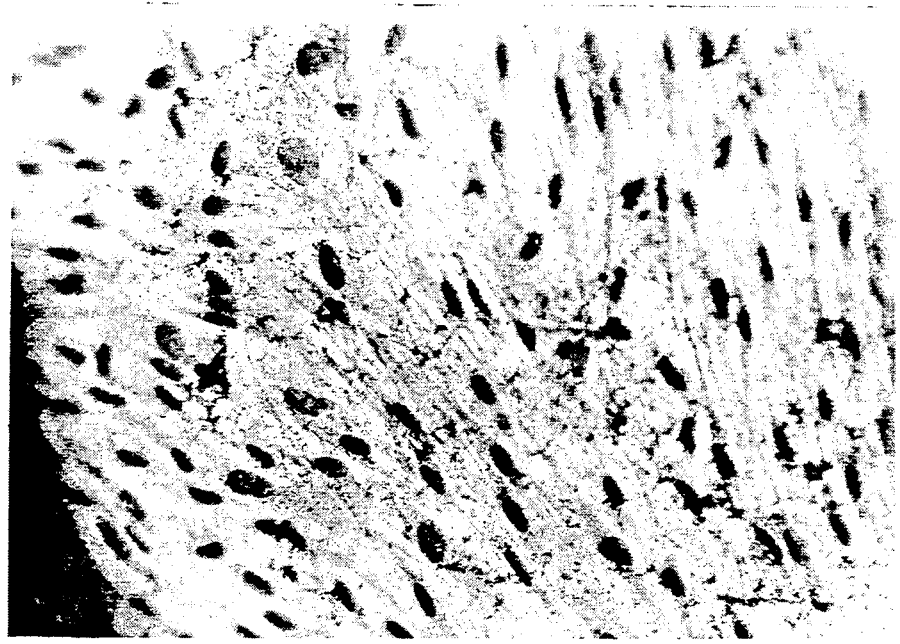

5. Phase-contrast microscopy of a carrier sample taken from the above reactor showed that the cells settle spread and grow evenly over both sides of the carrier (FIG. 8a and 8b).

6. Polystyrene cylinders or twisted ribbons having a glass roller bottle. $1 \times 10^7$ cells were seeded and the bottle was half filled with medium. The growth medium was replaced daily to avoid nutrient exhaustion. The cell proliferation was followed by removing periodically pieces of carrier and counting the cells after trypsinization. Cells proliferated with an average doubling time of 1.2-1.3 days and reached a constant level of $3-4 \times 10^4$ cells/cm$^2$ of carrier.

TABLE 1

Fibroblast adherence to polypropylene and polystyrene particles of various physical shapes

| Physical shape | Cell adhered 24 hrs. after plating (percent) | |
|---|---|---|
| | Polystyrene | Polypropylene |
| Short cylinders | 85 | 50 |
| Open cylinder segments | 90 | 60 |
| Cylindrical planar helix | 90 | 60 |
| Twisted squares | 95 | Not tested |
| Twisted ribbons | 98 | Not tested |

*Percent of control - Tissue culture petri-dishes

We claim:

1. A method of cultivating anchorage-dependent cells comprising the steps of forming a plurality of rectangles of plastics material; twisting said rectangles about a longitudinal axis of said rectangles; placing the rectangles in non-interconnected and random orientation within a cell cultivation vessel whereby cells may be cultivated in the vessel without nesting of the rectangles.

2. Apparatus for cultivation of anchorage-dependent cells comprising a cell cultivation vessel containing thin non-interconnected and randomly-oriented lengths of rectangles of plastics material twisted about the respective longitudinal axes of said rectangles whereby any tendency for nesting is countered.

* * * * *